United States Patent
Hernandez

(10) Patent No.: US 9,186,284 B1
(45) Date of Patent: Nov. 17, 2015

(54) HOLDER

(71) Applicant: Marlene Hernandez, Rosemead, CA (US)

(72) Inventor: Marlene Hernandez, Rosemead, CA (US)

(*) Notice: Subject to any disclaimer, the term of this patent is extended or adjusted under 35 U.S.C. 154(b) by 0 days.

(21) Appl. No.: 14/564,902

(22) Filed: Dec. 9, 2014

(51) Int. Cl.
*B65D 73/00* (2006.01)
*A61F 13/551* (2006.01)

(52) U.S. Cl.
CPC ....... *A61F 13/55175* (2013.01); *A61F 13/5514* (2013.01); *A61F 13/55145* (2013.01)

(58) Field of Classification Search
USPC ......................................................... 206/581
See application file for complete search history.

(56) References Cited

U.S. PATENT DOCUMENTS

| | | | | |
|---|---|---|---|---|
| 2,612,199 A * | 9/1952 | Schocket | | 150/112 |
| 2,764,201 A * | 9/1956 | Whippo | | 150/111 |
| 2,843,170 A * | 7/1958 | Frankfurt | | 150/112 |
| 4,286,639 A * | 9/1981 | Murphy | | 206/37 |
| 4,960,204 A * | 10/1990 | Young et al. | | 206/235 |
| 5,046,620 A * | 9/1991 | Barabino | | 206/581 |
| 6,039,175 A * | 3/2000 | Wright | | 206/37 |
| D427,424 S | 7/2000 | Conway | | |
| D432,784 S | 10/2000 | Conway | | |
| 6,446,688 B1 * | 9/2002 | Sutton | | 150/105 |
| 6,481,576 B1 * | 11/2002 | Watkins | | 206/440 |
| 8,251,113 B2 * | 8/2012 | Baxter | | 150/104 |
| 2002/0153074 A1 * | 10/2002 | Chen et al. | | 150/113 |
| 2006/0266663 A1 * | 11/2006 | Rhea | | 206/223 |
| 2007/0090014 A1 * | 4/2007 | Wheeler et al. | | 206/581 |
| 2011/0215025 A1 * | 9/2011 | Gonzales | | 206/581 |
| 2013/0062246 A1 * | 3/2013 | Staples | | 206/581 |
| 2013/0074997 A1 * | 3/2013 | Jones et al. | | 150/101 |

* cited by examiner

*Primary Examiner* — Jacob K Ackun

(74) *Attorney, Agent, or Firm* — Kenneth H. Ohriner; Perkins Coie LLP

(57) ABSTRACT

A holder for sanitary napkins may have a front panel and a rear panel connected via left and right side panels, and a top flap joined to the rear panel and attachable to an outside surface of the front panel, when the holder is in a closed position. One or two compartments are provided on an inner surface of the front panel, with additional compartments optionally on an inner surface of the rear panel. Each compartment may have a folding cover flap, and with each compartment adapted to hold a sanitary napkin. A center folder may be provided with additional compartments.

13 Claims, 7 Drawing Sheets

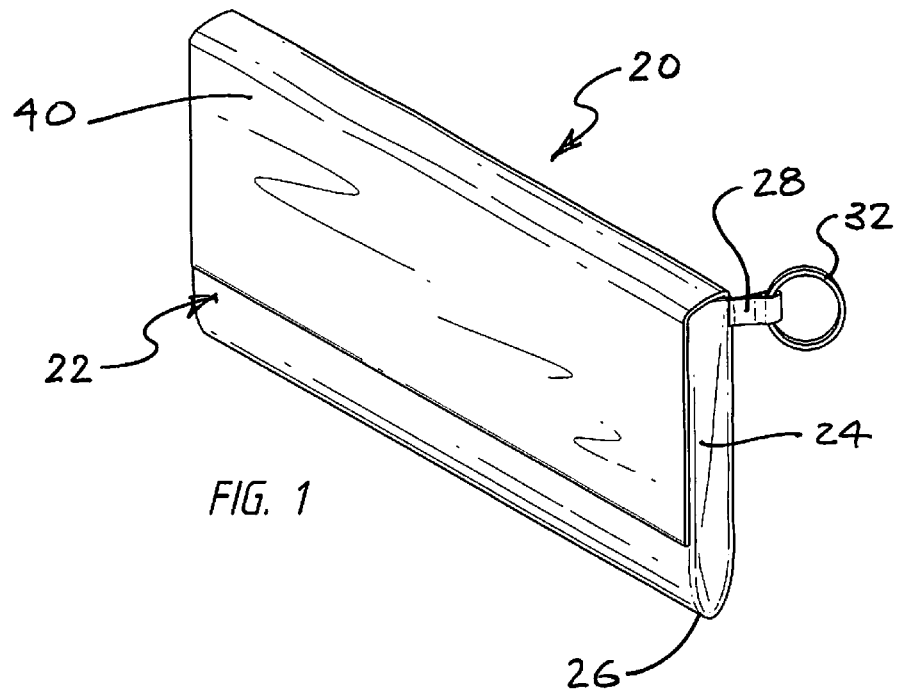
FIG. 1
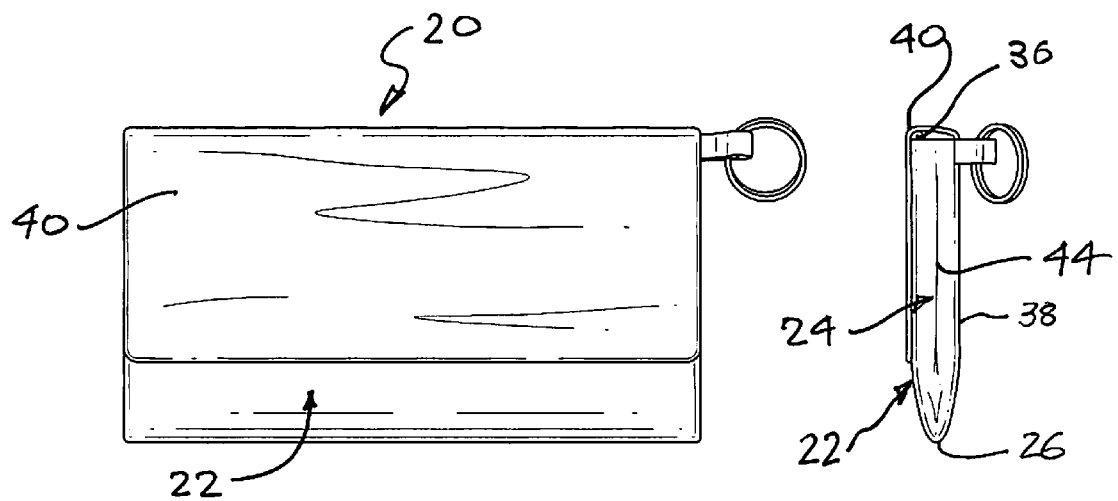
FIG. 2
FIG. 3

HOLDER

BACKGROUND OF THE INVENTION

The field of the invention is holders for feminine hygiene articles such as sanitary napkins and tampons.

Sanitary napkins and tampons are often carried loose in a hand bag, backpack or purse so that they will be available when needed. Although these products are generally provided within a package or wrapper, they may still get damaged or dirty over time, especially with repeated contact with keys, cosmetic cases, mobile phones, and other hard objects. These products may also be jumbled about in a hand bag and become difficult to find quickly when needed. Many users of sanitary napkins and tampons prefer to keep these products out of sight. When carried around loose in a hand bag, these products may be seen when the hand bag is opened in public, for example to get another object out of the bag. Hand bags are also increasingly subject to inspection at airports, government buildings, sports arenas, etc., revealing their contents to security officers and bystanders. Accordingly, there is a need for a holder for sanitary napkins and tampons that allows these products to be conveniently and discreetly carried and retrieved.

SUMMARY OF THE INVENTION

In a first aspect, a holder for sanitary napkins may have a front panel and a rear panel connected via left and right side panels, and a top flap joined to the rear panel and attachable to an outside surface of the front panel, when the holder is in a closed position. One or two compartments are provided on an inner surface of the front panel, with additional compartments optionally on an inner surface of the rear panel. Each compartment may have a folding cover flap, and with each compartment adapted to hold a sanitary napkin. A center folder may be provided with a bottom edge attachable to an inner surface on at least one of the front panel and the rear panel, with the center folder having, for example, a fifth compartment and a sixth compartment each adapted to hold a sanitary napkin.

In a second aspect, a holder for tampons has a front panel and a rear panel connected via left and right side panels. A top flap may be joined to or part of the rear panel and attachable to an outside surface of the front panel, when the holder is in a closed position. One or more tampon compartments are provided on an inner surface of the front panel, with additional compartments on an inner surface of the rear panel. In general, each of the compartments has a folding cover flap. When holding a tampon, the compartments may have a curved front surface. One or more fasteners may be associated with each flap, for holding the flap in a closed position.

Other objects and features will become apparent from the following description and drawings which disclose multiple embodiments of the invention, which are provided by way of example, and not as limiting on the scope of the invention.

BRIEF DESCRIPTION OF THE DRAWINGS

In the drawings, the same element number designates the same element in all of the views.

FIG. 1 is a front, top and right side perspective view of a holder for sanitary napkins, with the holder in a closed position.

FIG. 2 is a front view.

FIG. 3 is a right side end view.

DETAILED DESCRIPTION OF THE DRAWINGS

Figure 4:
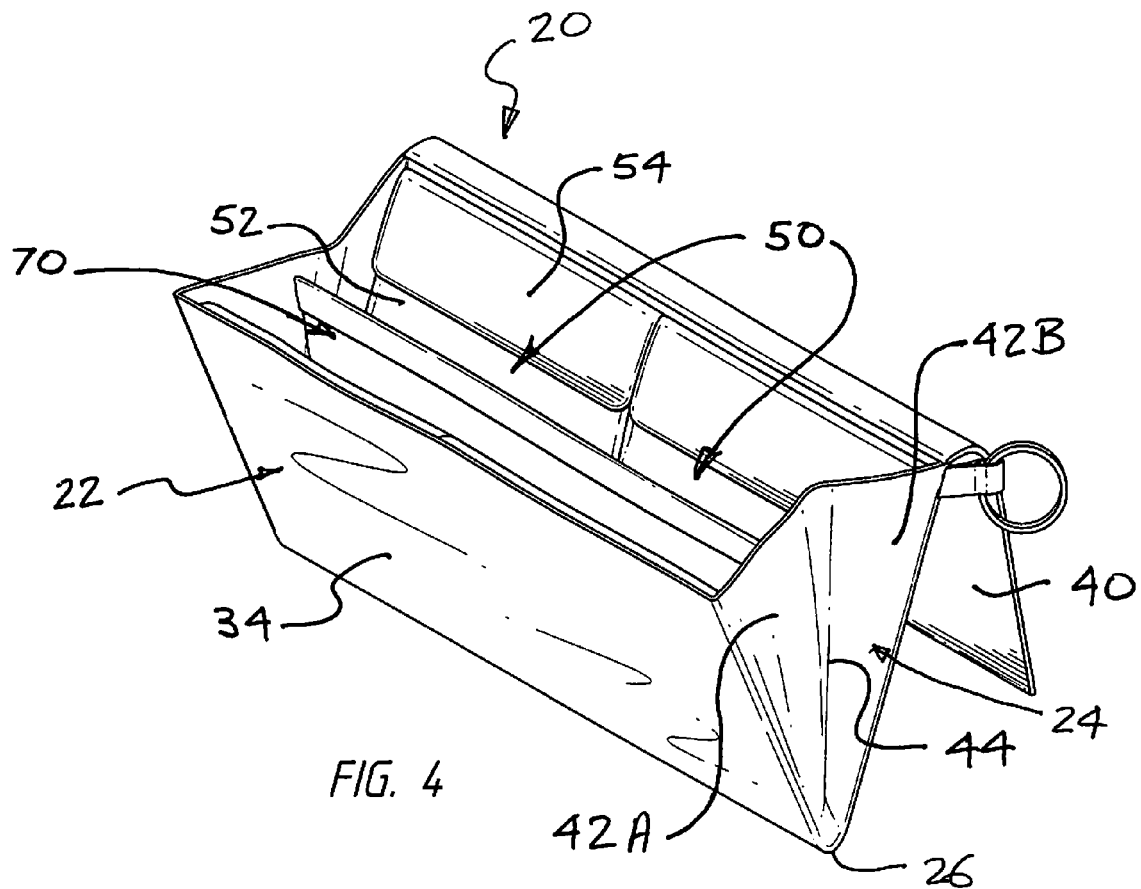
FIG. 4 is a view of the holder of FIG. 1 in an open position.

Turning now in detail to the drawings, as shown in FIGS. 1-5, a holder 20 for sanitary napkins has a body generally shown at 22 which may be described as having a front panel 34, a back panel 38, a bottom 26, and sides 24. A top flap 40 may be provided as an extension of the back panel 38. A tab 28 with a key ring 32 is optionally attached to the body 22, for example be sewing the tab 28 onto the back panel 38. Generally, the body 22 and its components may be made of leather, natural or synthetic fiber materials, or other flexible material. Nylon, polyester and other water proof or water resistant materials may be used. The components may be joined to form the body via sewing, adhesives, fasteners, or using other known techniques. As one example, the body 22 may be formed via a generally rectangular piece of material forming the top flap 40, the back panel 38 and the front panel 34, with the sides 24 joined to the piece of material. Alternatively, a single piece of material in an appropriate pattern may be used to provide all of the body and its components, with the material folded and attachments made as needed to form the body 22. This approach may reduce the amount of sewing or other attachments on the body 22.

Figure 5:
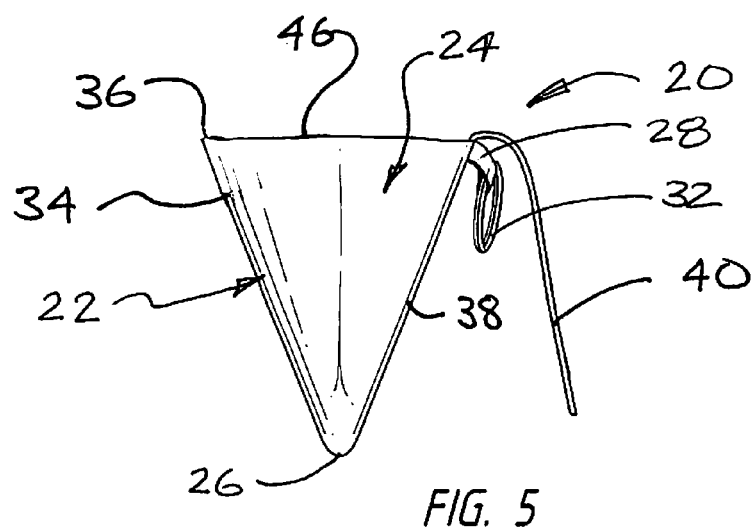
FIG. 5 is an end view of the holder of FIG. 4.

Referring to FIGS. 3 and 5, the upper edge of the front panel 34 may be folded over on itself to provide a rounded front edge 36. As shown in FIG. 4, the sides 24 may include first and second substantially triangular pieces 42A and 42B joined at a fold line 44. In this design, when the holder 20 is in the open position as shown in FIGS. 4-5, each side 24 has a generally triangular shape with a straight and flat top edge 46. In the closed position as shown in FIGS. 1 and 3, the sides 24 may flex inwardly at the fold line 44, to provide a compact configuration with a neat appearance. Each side 24 may alternatively be provided as a single piece of material having a crease, score or thinner middle area, rather than as separate pieces 42A and 42B.

Figure 6:
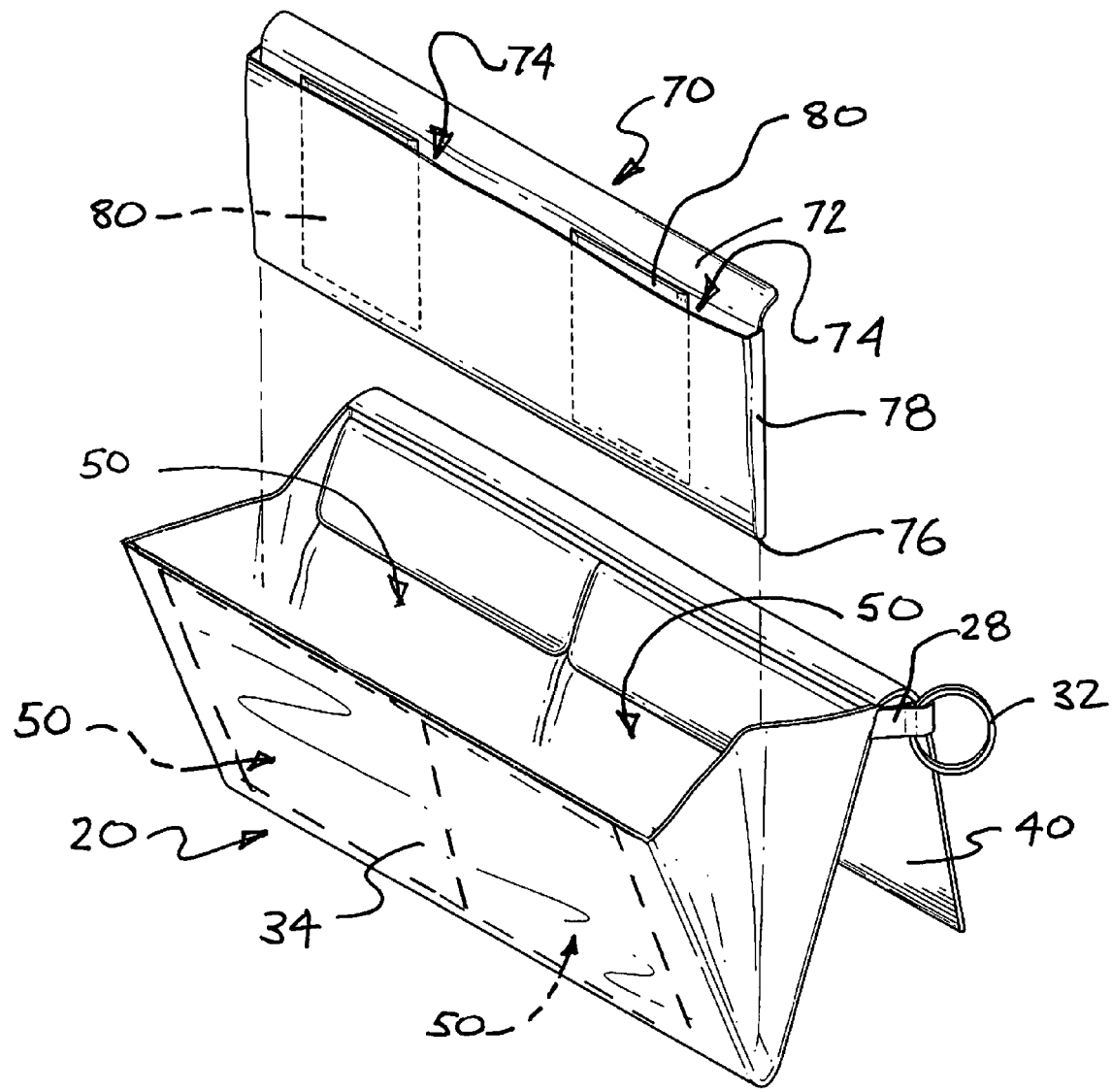
FIG. 6 is an exploded view of the holder of FIG. 4.
Figure 7:
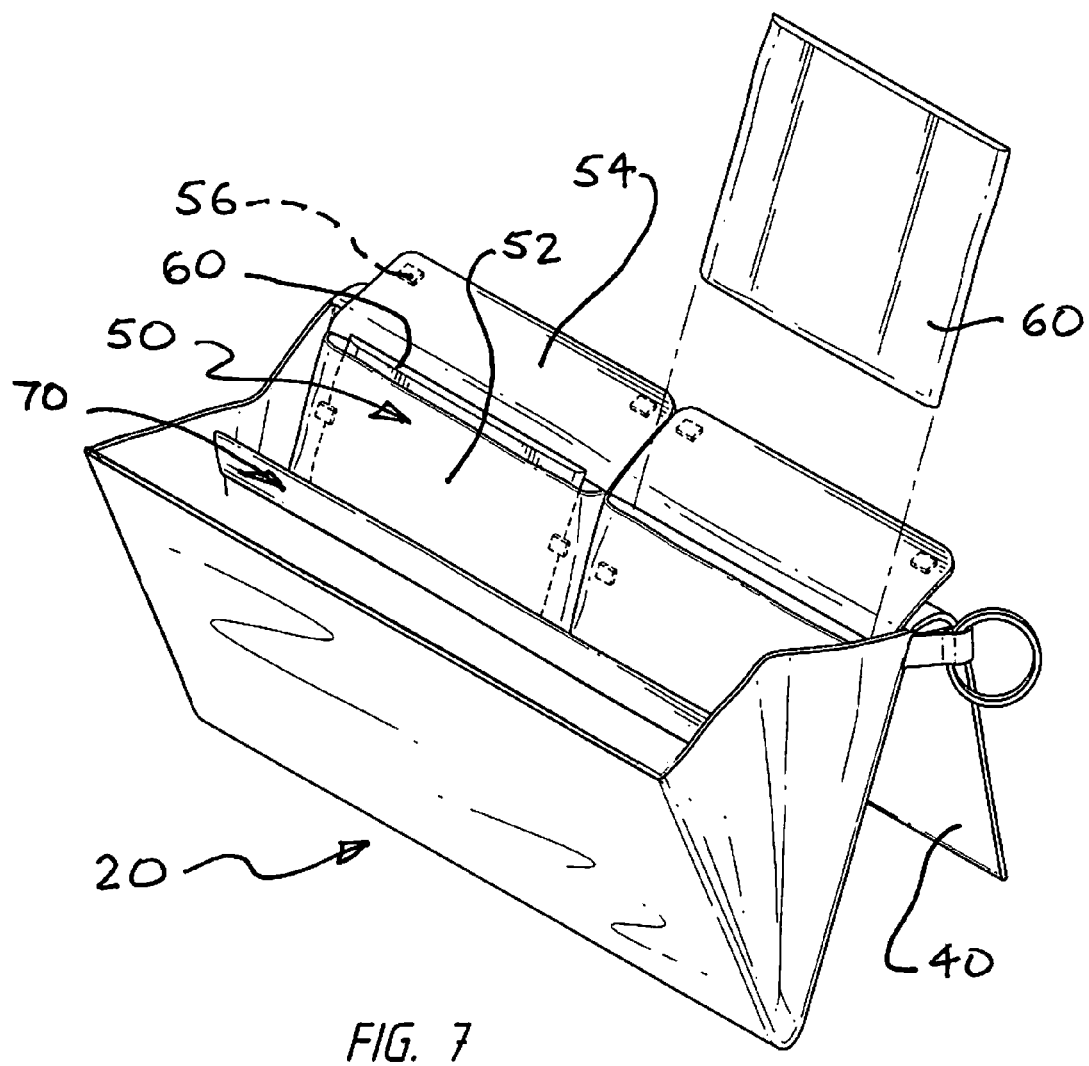
FIG. 7 shows the holder of FIG. 4 with a sanitary napkin removed.

As shown in FIGS. 4 and 6, napkin compartments 50 are provided within the holder 20, on the inner surface of the back panel 38 and of the front panel 34. Each compartment 50 may be formed via a square or rectangular piece of material sewn or otherwise attached along its left and right sides, and bottom, to the inside surface of the back panel 38 and the front panel 34, leaving an open top. Although the example of FIGS. 6 and 7 shows two compartments 50 on the back panel 38 and on the front panel 34, each panel may have a single compartment 50, or more than two compartments, depending on the size of the napkin to be carried.

Figure 12:
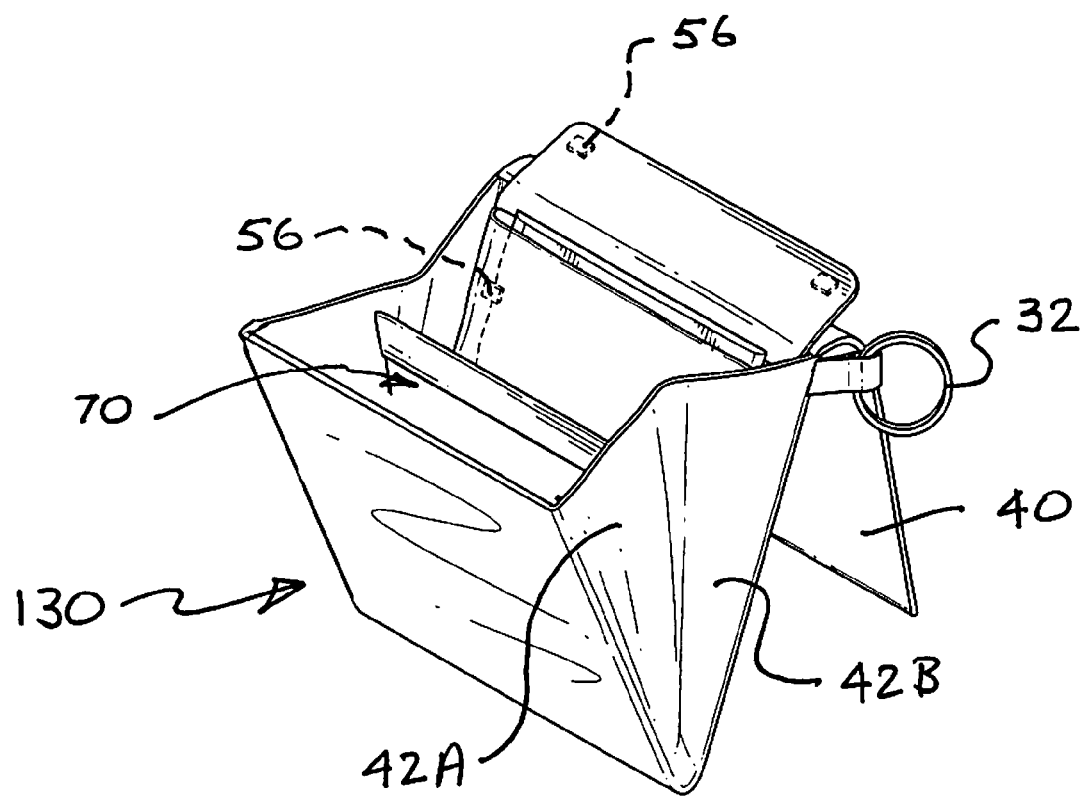
FIG. 12 is a front, top and right perspective view of another holder design, in an open position.

Sanitary napkins vary in size and shape, with a typical packaged napkin (shown at 60 in FIG. 7) about 6 to 10 cm long with a width of 6 to 8 or 10 cm. For use with napkins of this size, the dimensions of the compartments are nominally larger (e.g., 0.5 to 2 cm larger) in length and width than the packaged napkin. Consequently, the holder 22 for use with average sizes of napkins may have a length of about 12-20 cm and a width of about 6-12 cm. Referring to FIG. 12, an alternative compact size holder 130 may be designed to hold half as many napkins as the holder 20, while otherwise sharing the same design elements and concepts as the holder 20.

Turning again to FIGS. 6 and 7, a center folder or pouch 70 having front and back panels, sides 78, and optionally a top flap 72, may be provided within the holder 20. The center folder 70, if used, may have a bottom edge or fold 76 attached to an inner bottom surface of the holder 22, to permanently join the folder 70 to the holder 20. Alternatively, the sides 78 of the folder 70 may be attached to the sides 24 of the holder 20. The folder 70 may optionally be made to be removable from the holder 20.

The folder 70 may have compartments 74 for holding additional standard size sanitary napkins, or smaller and thinner so-called light-day napkins 80. In this case the compartments 74 are smaller than the compartments 50. Referring to FIG. 7, with the folder 70 included, the holder 20 in the example shown holds four standard size sanitary napkins 60 in four compartments 50, and two light-day napkins 80 in compartments 74.

Referring still to FIG. 7, a separate fold-over flap or cover 54 may be provided for each compartment 50. A single fold-over flap or cover 72 may be used on the folder 70. The covers 54 and 72 conceal the contents of the compartments 50 and 74, even when the holder 20 is open, allowing for more discrete use. One or more fasteners 56 may be associated with each cover. The fasteners may be snaps, Velcro hook and loop tape, magnets, or similar elements. FIG. 7 shows magnets used for the fasteners 56, with two magnets associated with each cover 54 and/or 70.

Magnets, if used, may be positioned under an overlying material layer so that they are not visible. In this design, the front wall 52 and the cover 54 of each compartment 50 may include two or more layers of material, with the magnets between the layers. Alternatively, the front wall 52 and cover 54 of each compartment may be a single layer of material, with a separate patch of material secured over each magnet fastener 56.

Figure 8:
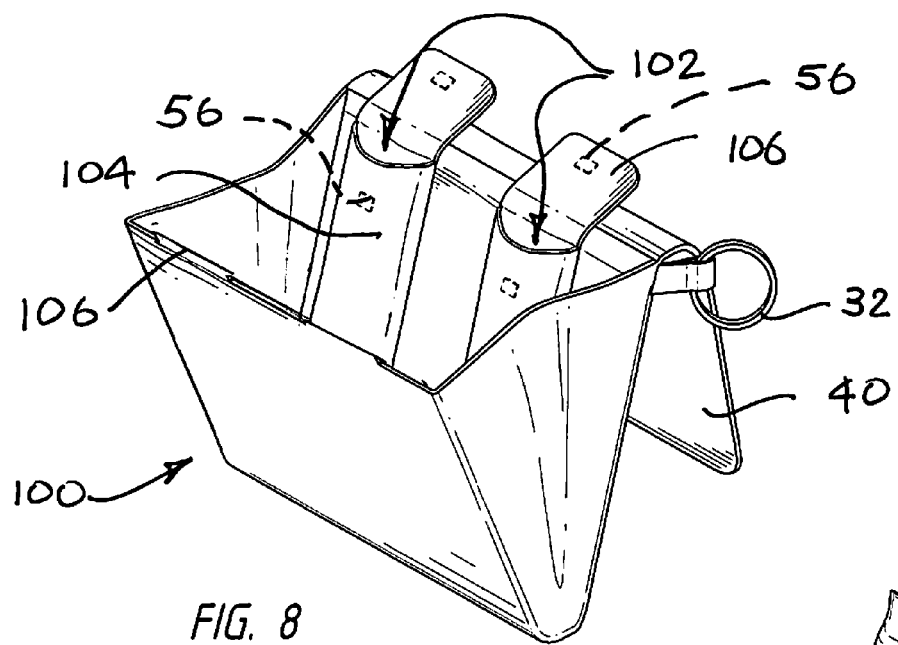
FIG. 8 is a front, top and right side perspective view of a second holder design for holding tampons, with the holder in an open position.
Figure 9:
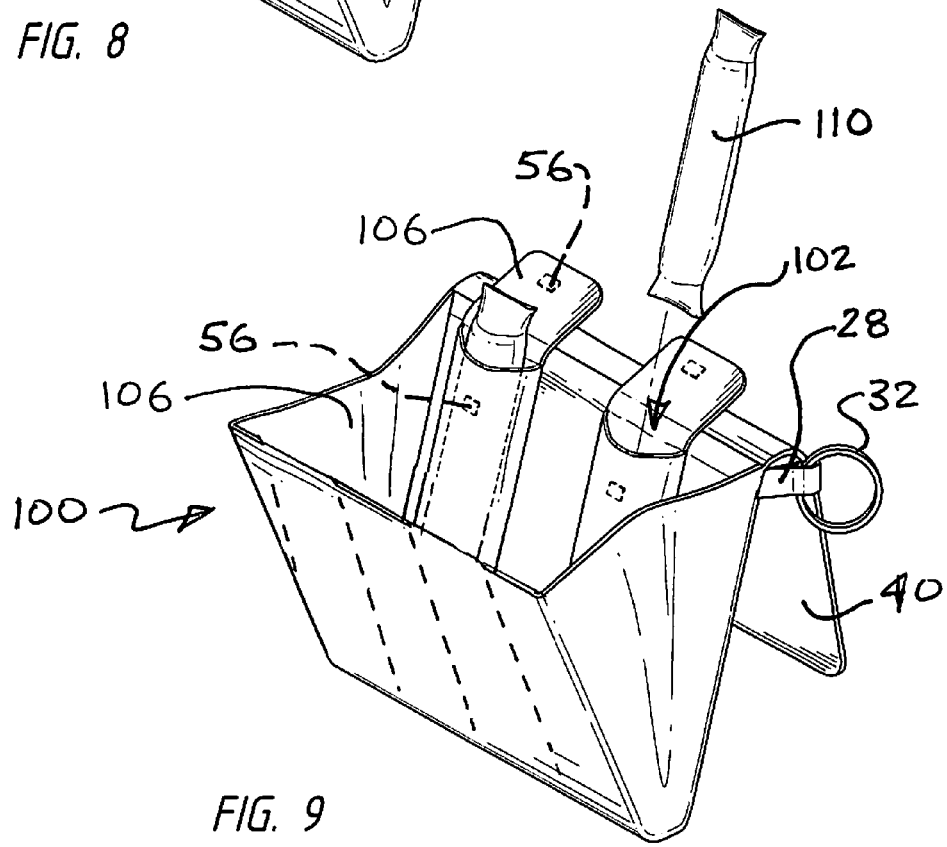
FIG. 9 shows the holder of FIG. 8 with a tampon removed.
Figure 10:
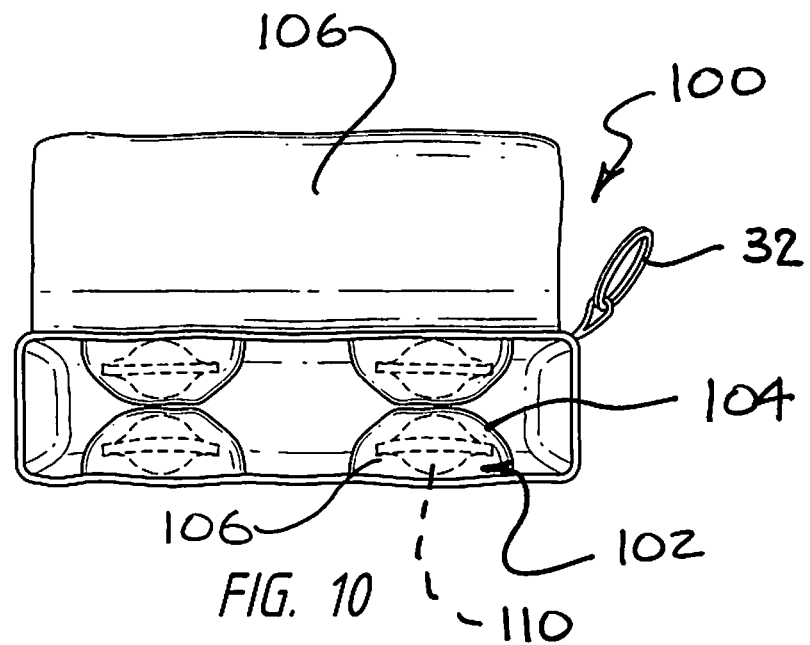
FIG. 10 is a top view of the holder of FIG. 8.

Turning now to FIGS. 8-10, another alternative holder 100 may have a body similar to the body 22 shown in FIGS. 1-7. However, the holder 100 has compartments 102 adapted for holding tampons 110. The tampon compartments 102 may have a flexible front wall 104 capable of conforming to the tubular shape of the tampon 110. For example, the front wall 104 may be a largely inelastic material, such as leather, cotton etc., with sufficient length to accommodate a tampon. The compartment 102 may optionally be partially elastic via use of a stretchable material, to exert a holding force on the tampon. Alternatively, the compartments 102 may have a more rigid semi-circular or curved shape, via use of curved or semi-circular cardboard or plastic inserts. The holders shown in FIGS. 1-10 may also be used for holding bladder control pads. The holders may also have an internal lining, optionally of an elastic material, with the internal lining stretching to accommodate a pad or napkin.

Figure 11:
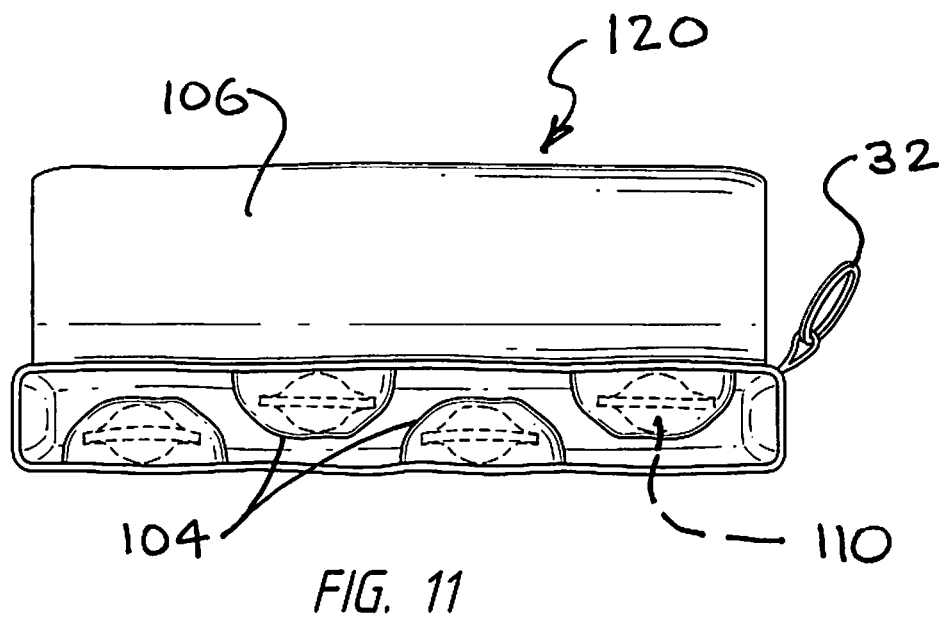
FIG. 11 is top view of a third holder design similar to the holder of FIG. 8.

Each compartment 102 may advantageously have a flap or cover 106 secured with a fastener 56 as described above. Alternatively, if the compartments 102 are made to positively secure the tampons in place, then the flaps 106 may be omitted. In the design of FIGS. 8-10, the compartments 102 on the front and back panels are aligned with each other. FIG. 11 shows modified design 120 with staggered compartments. The holder 120 may be thinner than the holder 100, and in some versions wider as well. Tampons vary in size. A typical tampon with an applicator tube in a package is about 9 to 13 cm long with a diameter of 1 to 2 cm. The compartments 102 are made nominally larger, although compartments using elastic materials may be nominally smaller. The holder of FIGS. 8-10 may also have an inner liner, optionally of an elastic material, which stretches to receive and hold a tampon. Each of the embodiments shown may optionally have a decorative design pattern on or in the material of the holder. Other decorative elements, e.g., beads, simulated jewels, etc. may be attached to the holders.

Each of the holders described may be modified to fit specific napkin and tampon size and shapes. Thus, novel holders have been shown and described. Various changes and substitutions may of course be made without departing from the spirit and scope of the invention. The invention, therefore, should not be limited, except to the following claims and their equivalents.

The invention claimed is:

1. holder for sanitary napkins, comprising:
a front panel and a rear panel connected via left and right side panels, with the left and right side panels each having a generally triangular shape and a top edge;
a top flap joined to the rear panel and attachable to an outside surface of the front panel, when the holder is in a closed position, with the left and right side panels folding inwardly as the holder is moved from an open position to a closed position, and with the top flap covering the top edges of the left and right side panels when the holder in the closed position;
first and second compartments on an inner surface of the front panel;
third and fourth compartments on an inner surface of the rear panel, with each of the first, second, third and fourth compartments having a folding cover flap, and with each adapted to hold a sanitary napkin; and
a center folder permanently attached to one or more of the front, rear, left side and right side panels, with the center folder having a fifth compartment and a sixth compartment each adapted to hold a sanitary napkin.

2. The holder of claim 1 with all of the panels and flaps comprising a flexible material.

3. The holder of claim 2 with the flexible material comprising leather, cloth or a synthetic fabric material.

4. The holder of claim 1 further including a tab attached to one or more panels, and a key ring on the tab.

5. The holder of claim 1 further comprising at least one fastener associated with each flap, for holding the flap in a closed position.

6. The holder of claim 5 where substantially each fastener comprises a magnet in a non-visible location.

7. The holder of claim 1 further including a first type of tampon having a thickness of at least 5 mm in the first, second, third and fourth compartments, and including a second type of tampon having a thickness of less than 5 mm in the fifth and sixth compartments.

8. A holder for tampons, comprising:
a front panel and a rear panel connected via left and right side panels, with the left and right side panels each having a generally triangular shape and a top edge;
a top flap joined to the rear panel and attachable to an outside surface of the front panel, when the holder is in a closed position, with the left and right side panels folding inwardly as the holder is moved from an open position to the closed position, and with the top flap covering the top edges of the left and right side panels when the holder in the closed position;
first and second compartments on an inner surface of the front panel;

third and fourth compartments on an inner surface of the rear panel, with each of the first, second, third and fourth compartments having a folding cover flap, and with each compartment having a curved front surface and a substantially flat rear surface forming a space between them for receiving a tampon; and at least one fastener associated with each folding cover flap, for holding the folding cover flap in a closed position.

9. The holder of claim 8 with substantially each fastener comprises a magnet in a non-visible location.

10. The holder of claim 8 with the front and rear panels and the top flap comprising a single piece of material.

11. The holder of claim 8 further including a tampon in each compartment.

12. The holder of claim 8 further including a tab attached to one or more panels, and a key ring on the tab.

13. A holder for sanitary napkins, comprising:

a front panel and a rear panel connected via left and right side panels, with the left and right side panels each having a generally triangular shape and a flat top edge;

a top flap joined to the rear panel and attachable to an outside surface of the front panel, when the holder is in a closed position, with the left and right side panels folding inwardly as the holder is moved from an open position to a closed position, and with the top flap covering the top edges of the left and right side panels when the holder in the closed position, and with all of the panels and flaps comprising a flexible material;

first and second compartments on an inner surface of the front panel;

third and fourth compartments on an inner surface of the rear panel, with each of the first, second, third and fourth compartments having a folding cover flap, and with each of the first, second, third and fourth compartments adapted to hold a sanitary napkin;

at least one fastener associated with each folding cover flap, for holding the folding cover flap in a closed position;

a center folder permanently attached to one or more of the front, rear, left side and right side panels having a bottom edge attachable to an inner surface on at least one of the front panel and the rear panel, with the center folder having a fifth compartment and a sixth compartment each adapted to hold a sanitary napkin; and a tab attached to one or more of the panels, and a key ring on the tab.

\* \* \* \* \*